United States Patent [19]
Dasher et al.

[11] 3,980,091
[45] Sept. 14, 1976

[54] QUATERNARY AMMONIUM COMPOUNDS IN PRETREATMENT OF HAIR BEFORE SHAMPOOING WITH AN ANIONIC SHAMPOO

[75] Inventors: George F. Dasher, Inverness; Kathleen A. O'Cull, Northlake; Thomas J. Schamper, Chicago, all of Ill.

[73] Assignee: Alberto Culver Company, Melrose Park, Ill.

[22] Filed: Jan. 6, 1975

[21] Appl. No.: 538,891

[52] U.S. Cl. .................. 132/7; 424/DIG. 1; 424/DIG. 2; 424/70; 424/71; 424/78
[51] Int. Cl.² ................ A45D 7/00; A61K 7/06
[58] Field of Search ........... 424/71, 78, 70, DIG. 2; 132/7

[56] References Cited
UNITED STATES PATENTS

| | | | |
|---|---|---|---|
| 3,723,325 | 3/1973 | Parran | 424/78 X |
| 3,740,422 | 6/1973 | Hewitt | 424/78 |
| 3,769,398 | 10/1973 | Hewitt | 424/70 |
| 3,862,310 | 1/1975 | Quasius | 424/70 |

*Primary Examiner*—Leonard Schenkman
*Assistant Examiner*—Vera C. Clarke
*Attorney, Agent, or Firm*—Wallenstein, Spangenberg, Hattis & Strampel

[57] ABSTRACT

This invention is concerned with the pretreatment of hair on the human head, preceding shampooing the hair with anionic type hair shampoos, and with compositions for effecting such pretreatment, to obtain highly improved manageability of the hair after shampooing and with improved fullness, combability and other desired properties of the hair. The pretreatment compositions utilize readily water-soluble quaternary ammonium compounds, particularly in combination with certain agents, notably polyethylenimines and N-ethanolacetamide, and desirably together with various supplemental ingredients.

18 Claims, No Drawings

QUATERNARY AMMONIUM COMPOUNDS IN PRETREATMENT OF HAIR BEFORE SHAMPOOING WITH AN ANIONIC SHAMPOO

This invention relates to improvements in the treatment of hair on the human head. As used hereafter, the term "hair" is to be understood to mean hair on the human head.

In connection with the treatment of hair, it has been a common practice, after washing or shampooing the hair, to subject it to various hair treatment compositions to impart certain desirable properties thereto. Among such hair treatment compositions, used after the washing or shampooing of the hair, are those commonly called, or characterized as, rinses and conditioners, which are formulated or designed to impart softness or smoothness of feel, luster, body or weight, manageability, combability and other properties to the hair. This is, in general, achieved by effecting a deposit on the hair of a film of a character such as serves, to some extent or other, to impart to the hair one or more of the above-stated properties or characteristics. The aforesaid hair treatment compositions may take various forms, such as aqueous or aqueous-alcoholic solutions, lotions, or dispersions; creams, etc.

Among such hair treatment compositions which have heretofore been known and some of which have been used to a substantial commercial extent are those of the type which contain cationic agents, generally of the quaternary ammonium type and exemplified by compounds such as cetyldimethylbenzyl ammonium chloride; cetyldimethylethyl ammonium chloride; stearyldimethylbenzyl ammonium chloride; distearyldimethyl ammonium chloride; laurylisoquinolinium bromide; and quaternary ammonium salts of homopolymers of dimethyl-or diethyl-aminoethyl methacrylate. Such hair treatment compositions are commonly compounded in the form of emulsions or dispersions and, as indicated above, they are applied to the hair after first washing the hair with a soap or a hair shampoo which commonly contains, as an ingredient thereof, soaps or anionic synthetic detergents, followed by thorough rinsing of the hair with water, after which the aforesaid hair treatment compositions are applied to the hair. The thorough rinsing of the hair with water is effected to remove as much of the soaps or anionic detergents as possible since, otherwise, precipitates form in the hair by virtue of the incompatibility of the cationics with the anionics.

Cationic agents are known generally to be substantive to the hair and, therefore, in the use of the above-mentioned hair treatment compositions which contain cationic agents, a film or deposit is formed on the hair shafts, by adsorption, and due to reaction between the cationic agent and the keratinous material of the hair. The character and the amount of such film as is formed and deposited on the hair influence the properties and characteristics of the hair.

The foregoing known practices serve a distinctly useful purpose and, in general, are reasonably effective in imparting to the hair, to at least a fairly good extent, properties and characteristics of the nature described above. They are frequently, however, less effective than is desired, particularly with respect to the matter of control of the weight of the hair and its manageability.

The present invention is based upon discoveries which have been made which enable more effective management of the hair with excellent and improved results in one or more respects with regard to body or weight control, combability, fluffiness and spring and, in general, desired configuration control of the hair.

In accordance with the present invention, the hair is first treated with an aqueous composition which contains certain types of quaternary ammonium compounds and thereafter, without intermediate rinsing, is washed with soap or, more desirably, with a formulated shampoo of the type which contains an anionic cleanser or detergent such as soaps and/or anionic synthetic detergents, all as is described in detail below. It may, however, here be observed, and as will be noted further below, that no novelty is claimed broadly in the practice of treating hair first with an agent which has cationic properties and then followed by washing the hair with a shampoo containing an anionic detergent.

Pursuant to the present invention, the hair pretreatment composition, which is applied to the hair prior to the washing step with soap or shampoo containing soap and/or an anionic synthetic detergent, comprises an aqueous composition which contains a readily water-soluble quaternary ammonium compound whose solubility is such that, in water at room temperature, it forms a solution, in use concentrations of at least 0.5%, by weight of the solution, which is clear to the naked eye. Since the use concentration of the quaternary ammonium compound may be as high as about 4%, by weight of the solution, those quaternary ammonium compounds which are utilized in such concentrations should have water solubilities such that, when looked at with the naked eye, they appear to be clear, even though, in actual fact, micelles or agglomerates may be present which would establish that the apparently clear solution is not a true solution. For the purposes of the present invention, reference to a clear solution means a solution which is optically clear to the naked eye unaided by sophisticated optical instruments.

While, as stated above, the quaternary ammonium compounds which are used in the hair pretreatment compositions of the present invention should have the solubility characteristics to form clear solutions in water at room temperature at the use concentrations, in the range of 0.5 about 4%, and while the finished hair pretreatment compositions as commercially marketed are most desirably in the form of clear aqueous solutions, the hair pretreatment compositions can be made up in other forms, for instance, as cream products, with the use of acid-stabilized glyceryl monostearate or other agents. However, since the hair, after the application thereto of the pretreatment composition, and without intermediate rinsing, is to be washed with soap or with a shampoo containing soaps and/or anionic synthetic detergents, ingredients should not be included in the pretreatment composition which would unduly interfere with or cause undue difficulties in the washing step with the soap or said hair shampoos.

In addition to possessing the water solubility discussed above, the quaternary ammonium compounds should also contain one long chain alkyl radical attached to the central nitrogen atom of the quaternary ammonium compound. The long chain alkyl radical should be selected so that it does not result in loss of the stated water-solubility properties desired in the quaternary ammonium compound. Hence, while, in general, the long chain alkyl radical may contain from 8 to 18 carbon atoms, it is particularly desirable that it contain from 10 to 14 carbon atoms, and, better still, predominately 12 carbon atom in most cases. The absence of a long chain radical, or the substantial equivalent thereof as noted below, will result in an inadequately satisfactory coating on the hair shaft and an unsatisfactory coating or deposit in the pores or crevices or on the hair shaft after the shampooing step, as hereafter pointed out.

At least most of the quaternary ammonium compounds, which are useful in the production of the hair pretreatment compositions of and used in practicing the present invention, can be represented by the formula

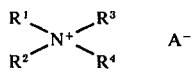

where $R^1$ is a $C_8$–$C_{18}$, particularly $C_{10}$–$C_{14}$ with $C_{12}$ predominating, alkyl radical; each of $R^2$, $R^3$ and $R^4$ is a $C_1$–$C_3$ alkyl radical, particularly a methyl radical; and the total of the number of carbon atoms in $R^2$, $R^3$ and $R^4$ generally, and most desirably, should not exceed 6; and A is an innocuous inorganic or organic anion, particularly halogen such as chlorine or bromine, but which may also be other anions such as sulfate, sulfite, phosphate, nitrate, nitrite, acetate, methylsulfate, and toluenesulfonate.

Illustrative examples of such quaternary ammonium compounds are octyltrimethyl ammonium chloride; decyltrimethyl ammonium chloride; lauryldimethylethyl ammonium chloride; dodecyltrimethyl ammonium chloride; tetradecyltrimethyl ammonium chloride; hexadecyltrimethyl ammonium chloride; octadecyltrimethyl ammonium chloride; mixed higher alkyl trimethyl ammonium chlorides containing mixtures of predominately $C_8$–$C_{18}$ alkyl radicals such as are derived from sources such as coconut oil or special fractions thereof high in $C_{12}$, soya bean oil, cottonseed oil, babassu oil, palm oil, etc.; and corresponding compounds wherein the anion is other than halogen, as noted above.

To obtain the desired good solubility in water of the quaternary ammonium compounds, there should be only one $C_8$–$C_{18}$ alkyl group in the compounds. However, quaternary ammonium compounds with suitable solubility can be used such as dihexyldimethyl ammonium chloride or bromide, or similar compounds with anions other than chlorine or bromine. Quaternary ammonium compounds in which all of the alkyl groups are of low molecular weight, such as tetramethyl — or tetraethyl ammonium chloride or bromide are unsatisfactory because, while they are very soluble in water, they do not form a satisfactory film on the hair and do not adequately "weight" the hair, and, in any event, they do not impart the desired properties to the hair such as are achieved through the use of compounds such as, for instance, dodecyltrimethyl ammonium chloride or bromide when used in accordance with the practice of the present invention.

Various other quaternary ammonium compounds, which do not fall within the scope of the foregoing formula, which formula encompasses the particularly desirable compounds for use in the practice of the present invention, can, nevertheless, be used with reasonably good results, illustrative examples of which are long chain or $C_8$–$C_{18}$ alkyldimethylbenzyl ammonium chlorides such as dodecyldimethylbenzyl ammonium chloride; tetradecyldimethylbenzyl ammonium chloride; cetyldimethylbenzyl ammonium chloride; dodecylpyridinium chloride; cetylpyridinium chloride; n-dodecyldimethyl-p-chlorobenzyl ammonium chloride; N-(lauroylcolaminoformylmethyl)-pyridinium chloride; diisobutyl-phenoxyethyldimethylbenzyl ammonium chloride; 9-octadecenyldimethylethyl ammonium chloride; myristyl-r-picolinium chloride; diisobutylcresoxyethyldimethylbenzyl ammonium chloride; and amine oxides such as dodecyldimethylamine oxide; dodecyldiethylamine oxide; and 9-octadecenyldimethylamine oxide; which amine oxides, under certain known acid conditions, are converted into or function as quaternary ammonium compounds.

It will be understood that any two or more of the foregoing, or other, quaternary ammonium compounds can be used so long as they meet the criteria set forth above and are not mutually incompatible.

In place of the foregoing quaternary ammonium compounds, the corresponding sulfonium and the corresponding phosphonium compounds can be used with at least fair results but, for a variety of practical reasons, they are of distinctly secondary significance.

It is especially advantageous, in the more important embodiments of the present invention, to utilize, in conjunction with the quaternary ammonium compounds in the hair pretreatment compositions, minor proportions of (a) N-ethanolacetamide or lauric ethanolamide or coconut oil mixed fatty acid ethanolamides, and (b) polyethylenimines.

The aforesaid (a) ingredient has heretofore been used in hair treatment compositions and no novelty is claimed broadly in its use in the treatment of hair. It serves to aid in the retention by the hair of a certain amount of water and plays a role in the control of hair weight or the weight of the filmed hair.

The polyethylenimines, which are made by polymerizing ethylenimine, may be used in the form of ethylenimine polymers, or polyethylenimines, of variable molecular weights, advantageously of the order of M.W. about 10,000 to about 70,000, with a good average in the range of about 40,000 to about 60,000. In conjunction with the quaternary ammonium compounds they cooperate and function to form a coating or film on the hair shafts of a character such that exceptional manageability or control and luster and natural appearance are imparted to the hair after the step of washing the hair with the soap or anionic shampoo is effected followed by rinsing out the soap or shampoo with water.

It may also be noted that no novelty is claimed in the use, broadly or per se, of polyethylenimines of varying molecular weights, including molecular weights of the order of 60,000, for the treatment of hair. Thus, they have been used in hair shampoos to obtain increased sheen, body and manageability of the hair and improved combability. They have also been used in treating hair prior to washing or shampooing the hair with anionic shampoos. It is known that the polyethylenimines are themselves cationic in character under certain conditions and are substantive to hair. However, it has been found that the objectives behind their use, in hair shampoos or for treating hair prior to shampooing with soap or anionic shampoos, are inadequately achieved. Tests carried out with the washing or shampooing of hair with anionic detergent shampoos containing added polyethylenimines, as well as tests carried out by pretreatment of hair using polyethylenimines alone followed by washing with soap or with anionic shampoos, have given results which have left much to be desired. Used in conjunction with the quaternary ammonium compounds in a pretreatment of the hair, followed by washing or shampooing with soap or anionic detergent shampoos, according to the present invention, the results obtained have been markedly superior.

The particularly important aspects of the present invention, therefore, involve the utilization, for the pretreatment of the hair, of aqueous compositions, and especially clear solutions, containing water-soluble quaternary ammonium compounds in conjunction with polyethylenimines, and most desirably also in conjunction with N-ethanolacetamide or the aforesaid ethanolamides, and the proportions involved will generally fall within the following approximate ranges in terms of % by weight of the pretreatment compositions:

|  | % |
| --- | --- |
| Quatenary ammonium compound | 0.5 to 4 |
| Polyethylenimine | 0.2 to 5 |
| N-Ethanolacetamide or ethanolamide | 3 to 18 |
| Water | 70 to 90 |

A preferred range of proportions is 1.5 to 2.5%, generally about 2%, of the quaternary ammonium compound; 0.4 to 2%, generally about 0.5 to 1.5%, of the polyethylenimine; 3 to 18%, generally about 4 to 15%, of the N-ethanolacetamide or ethanolamide; and the balance very predominately water, generally from about 70 to about 85%, preferably about 75%.

Supplemental agents may and, generally, are desirably included in the hair pretreatment compositions such as, for instance, one or more of thickeners or viscosity modifiers, proteins, silicone hair lubricants, preservatives, perfumes, solubilizers for said perfumes, coloring agents, etc.

In those instances in which polyethlenimines are utilized in the hair pretreatment compositions in conjunction with the quaternary ammonium compounds, which, as indicated above, represent particularly important embodiments of the present invention, it is highly desirable, for insuring clarity of the pretreatment compositions, to add particular types of acids to the compositions. Without the addition of an acid, the pH of the compositions will commonly be weakly basic. The addition of low molecular weight monobasic organic acids, particularly formic acid or acetic acid, in amounts to reduce the pH of the composition to the order of about 3.2 to about 3.7, optimally about 3.5, leaves solutions which are clear to the naked eye. While other acids can be used, such as tartaric acid or citric acid or phosphoric acids, or other water-soluble polybasic acids, to produce solutions which have an acid pH of the general order indicated above, their use is not preferred because they tend to produce solutions which are not clear and are of generally turbid character. The pretreatment compositions will generally be formed so as to have a pH from about 3 to below 7, with a range of about 3.5 to 6.0 being generally most desirable.

The following examples are illustrative of hair pretreatment compositions which are useful in the practice of the present invention. Other compositions can readily be prepared in light of the disclosures and guiding principles and teachings provided herein. All numerical values represent percentages by weight of the compositions, and reference to "Balance" means the weight of the water to bring the composition to 100%.

EXAMPLE 1

| Arquad C-50 (50% active)[1] | 4.0 |
| --- | --- |
| N-Ethanolacetamide | 15.0 |
| Polyethylenimine (60,000 M.W.) (40% active) | 1.25 |
| Volpo 20[2] | 2.0 |
| Formic acid (90% active) | 1.4 |
| Cellosize QP 100 MH[3] | 0.37 |
| Methyl Paraben[4] | 0.1 |
| Perfume | Q.v. |
| Water (deionized) | Balance |

[1]Coco trimethyl ammonium chloride
[2]Nonionic emulsifier to solubilize perfume
[3]Nonionic thickener
[4]Preservative (methyl ester of p-hydroxy benzoic acid)

There is nothing critical about the order of mixing of the ingredients. They may simply be admixed in the water, under conditions of stirring or agitation, heating slightly, if desired, to hasten the formation of the solution, which, especially desirably, is clear to the naked eye. Generally, the perfume, where used, is added after the other ingredients have been dissolved.

EXAMPLE 2

| Arquad C-50 (50% active) | 4.5 |
| --- | --- |
| N-Ethanolacetamide | 15.0 |
| Polyethylenimine (60,000 M.W.) (40% active) | 1.5 |
| Volpo 20 | 2.0 |
| Formic acid (90% active) | 1.4 |
| Cellosolve QP 100 MH | 0.37 |
| Methyl Paraben | 0.1 |
| Perfume | Q.v. |
| Water (deionized) | Balance |

EXAMPLE 3

| Arquad C-50 (50% active) | 4.0 |
| --- | --- |
| N-Ethanolacetamide | 15.0 |
| Polyethylenimine (60,000 M.W.) (40% active) | 1.5 |
| Volpo 20 | 2.0 |
| Orthophosphoric acid (75%) | 0.5 |
| Cellosize QP 100 MH | 0.37 |
| Methyl Paraben | 0.1 |
| Perfume | Q.v. |
| Water (Deionized) | Balance |

EXAMPLE 4

| Arquad C-50 (50% active) | 4.0 |
| --- | --- |
| N-Ethanolacetamide | 5.0 |
| Polyethylenimine (60,000 M.W.) (40% active) | 1.25 |
| Volpo 20 | 2.0 |
| Formic acid (90% active) | 1.15 |
| Cellosolve QP 100 MH | 0.37 |
| Methyl Paraben | 0.1 |
| Perfume | Q.v. |
| Water (deionized) | Balance |

EXAMPLE 5

| Arquad C-50 (50% active) | 4.0 |
| --- | --- |
| N-Ethanolacetamide | 15.0 |
| Polyethylenimine (60,000 M.W.) (40% active) | 1.25 |

-continued

| | |
|---|---|
| Volpo 20 | 2.0 |
| Formic acid (90% active) | 1.15 |
| Cellosolve QP 100 MH | 0.37 |
| Methyl Paraben | 0.1 |
| Perfume | Q.v. |
| Water (deionized) | Balance |

EXAMPLE 6

| | |
|---|---|
| Arquad C-50 (50% active) | 4.0 |
| Polyethylenimine (60,000 M.W.) (40% active) | 1.5 |
| Volpo 20 | 0.2 |
| Orthophosphoric acid (75%) | 0.5 |
| Cellosolve QP 100 MH | 0.1 |
| Methyl Paraben | 0.1 |
| Dow-Corning 472 Silicone Fluid | 1.0 |
| Perfume | Q.v. |
| Water (deionized) | Balance |

EXAMPLE 7

| | |
|---|---|
| Arquad C-50 (50% active) | 4.0 |
| N-Ethanolacetamide | 12.0 |
| Cellosize PQ 100 MH | 0.35 |
| Methyl Paraben | 0.1 |
| Water (deionized) | Balance |

EXAMPLE 8

| | |
|---|---|
| Dodecyldimethylbenzyl ammonium chloride | 2.0 |
| N-Ethanolacetamide | 10.0 |
| Polyethylenimine (60,000 M.W.) (40% active) | 1.2 |
| Acetic acid | 1.0 |
| Perfume | Q.v. |
| Water (deionized) | Balance |

EXAMPLE 9

| | |
|---|---|
| Cetylpyridinium chloride | 1.8 |
| N-Ethanolacetamide | 4.5 |
| Polyethylenimine (40,000 M.W.) (40% active) | 1.7 |
| Formic acid (90% active) | 1.1 |
| Water (deionized) | Balace |

EXAMPLE 10

| | |
|---|---|
| Lorol triethyl ammonium chloride | 2.0 |
| N-Ethanolacetamide | 12.0 |
| Polyethylenimine (60,000 M.W.) (40% active) | 1.3 |
| Formic acid (90% active) | 1.4 |
| Cellosize QP 100 MH | 0.3 |
| Water (deionized) | Balance |

The hair pretreatment compositions, as noted above, are most desirably marketed and used in the form of aqueous solutions and are dispensed from conventional non-pressurized containers. If desired, they can also be packaged in atomizer containers or in conventional aerosol pressure packages using volatile liquid propellants such as the well known "Freons."

In the treatment of the hair, in accordance with the present invention, as indicated above, the pretreatment quaternary ammonium composition is applied to the hair and distributed therethrough reasonably thoroughly and uniformly, in any suitable or convenient manner, as, for instance, by rubbing with the fingers. Then, promptly, or after waiting, if desired, for a convenient time but most desirably while the hair is still wet, it is washed, in conventional manner, with a soap or with a shampoo containing a soap and/or a synthetic anionic detergent. Any of numerous known and commercially marketed soaps or shampoos, in liquid, cream or paste form, can be employed comprising or containing, for instance, water-soluble soaps such as coconut oil fatty acid soaps or water-soluble synthetic anionic detergents such as primary long chain alkyl sulfate salts exemplified by sodium lauryl sulfate or triethanolamine lauryl sulfate or other salts of lauryl sulfate; or salts of long chain alkylbenzene sulfonic acids such as sodium or triethanolamine salts of linear or branched chain dodecylbenzene sulfonic acids; salts of sulfated monoglycerides such as sodium, ammonium and alkanolamine salts of coconut oil mixed fatty acid monoglycerides; salts of sulfated tridecyl alcohol; or other known anionic synthetic detergents conventionally used in anionic detergent-containing shampoos. The soap or shampoo is then thoroughly rinsed away with water in the usual manner. The hair is then ready to be combed and set or shaped as may be desired.

By employing quaternary ammonium compounds of the character described above in the pretreatment step, a substantial quantity of the quaternary ammonium compound penetrates into the scalp area and permeates the hair deeply and quickly and is deposited as a film through its substantive action on the hair. Where a polyethylenimine is utilized in the pretreatment composition, it contributes its effect, also, in the formation of a film on the hair. At any rate, the film formation occurs quickly throughout the body of the hair around the hair shafts, and also in the areas, particularly the deeper areas closely adjacent the scalp proper, and also where the hair may have been or has previously been damaged due to other treatments and where, therefore, there may be internal voids or crevices in the hair shafts. The films which are formed as a result of the pretreatment, or which form and are present as a result of the subsequent reaction with soap or anionic synthetic detergent in the subsequent washing or shampooing step, appear to exert a favorable effect in the direction of repair or alleviation of damaged hair shafts.

After the washing or shampooing of the pretreated hair and the subsequent rinsing with water, it appears that appreciable filmed hair shafts remain, particularly in the cracks and crevices, indeed to a greater extent than is the situation with prior known practices in the art, and which are of a character such that, overall, the improvements which result from the practice of the present invention are achieved or brought about.

By way of further explanation, it may be pointed out that it is desirable to maintain long chain-or fatty chain-containing substances within cracks and crevices of individual hair strands. These cracks and crevices generally develop during the process of combing, curling, brushing and application of other cosmetic treatments to the hair. They are the physical result which is involved in hair damage. The presence of these fatty deposits within the hair strand make it more supple, less brittle, and thus, helps to prevent further breakage on combing.

It is important, to the practice of the present invention for most effective results, to get deep penetration during the short time available in treating hair under practical conditions. By making use of small, water-soluble, rapidly diffusing quaternary ammonium molecules at the first stage, as distinguished from polymeric cationic substances or high molecular weight relatively poorly water-soluble substances such as, for instance, distearyldimethyl ammonium chloride, generally maximal penetration of the hair shaft is effected. Then, in the subsequent shampooing step, where anionic shampoos are used, and particularly where they are water-soluble and have molecular weights of the general order of those of the water-soluble quaternary ammonium compounds used in the pretreatment step, or somewhat higher or somewhat lower molecular weights than that of said quaternary ammonium compounds, deep penetration of said anionic material into the hair shaft also appears to take place. When the quaternary ammonium compound and the anionic detergent come into contact, a reaction takes place resulting in the formation of a double long chain-or fatty-chain like salt which is essentially insoluble in the rinse water and remains in place within, and, generally relatively deeply within, the hair shaft.

Polymeric cationic materials and other cationic materials of unduly high molecular weight diffuse, at best, very slowly into hair strands. Hence, deposition of such cationic materials is not specific to the deep cracks and crevices in the hair strands but, on the contrary, tends to become relatively uniformly distributed over the hair, an effect which is undesirable. Thus, for instance, coating the surface of the hair with a cationic polymer tends to weight down individual hair strands. This added weight tends to make the hair flatter from the scalp and resembles in appearance the effect of dirt on the hair.

In the practice of the present invention, the reaction product which results between the water-soluble quaternary ammonium compound and the anionic detergent of the shampoo, under the particular conditions under and in the environment in which it is formed, is beneficial to the objectives of the invention. Thus, when in contact with the large amounts of anionic materials in the shampooing step, the reaction product formed from said anionic material and the water-soluble quaternary ammonium compound from the pretreatment step, is solubilized into the aqueous phase. Deeply imbedded material does not tend to come in contact with excess anionic during the shampooing process. However, material deposited in more available locations such as the hair shaft surface is solubilized and removed during the shampoo process. As a consequence, only the deeply imbedded material remains in the hair after the shampoo process. In essence, the "repair" material is deposited efficiently where it is needed without the negative effect of having too much material left on the hair as is the case when a cationic polymer is used. In other words, both the water-soluble quaternary ammonium compound and the water-soluble anionic detergent are able to penetrate deeply into the hair shaft. There they form an insoluble compound which stays in place through many later shampoos, adding body and suppleness to the hair strand.

For convenience of expression, the term "anionic" shampoo is used in the claims to mean soaps, as well as shampoos for washing the hair in which the shampoos contain as an essential cleanser or detergent one or more soaps and/or anionic synthetic detergents, with or without various additional or supplemental ingredients illustrative of which are nonionic surfactants, alkanolamides, thickeners, etc.

What is claimed is:

1. A method of treating hair to improve the manageability thereof, which comprises initially contacting the hair with a dilute aqueous composition containing a water-soluble quaternary ammonium compound containing at least one long chain alkyl radical attached to the central nitrogen atom thereof, and then shampooing the hair with an anionic shampoo.

2. The method of claim 1, in which the quaternary ammonium compound has the formula

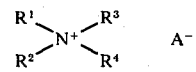

wherein $R^1$ is $C_8$–$C_{18}$ alkyl; each of $R^2$, $R^3$ and $R^4$ is $C_1$–$C_3$ alkyl, the total number of carbon atoms in $R^2$, $R^3$ and $R^4$ not exceeding 6; and A is an innocuous anion.

3. The method of claim 1, in which the dilute aqueous composition containing the quaternary ammonium compound also contains at least one member of the group of N-ethanolacetamide and a fatty acid ethanolamide in which the fatty acid comprises predominately lauric acid.

4. The method of claim 1, in which the dilute aqueous composition containing the quaternary ammonium compound also contains polyethylenimine having a molecular weight between about 10,000 and about 70,000.

5. The method of claim 3, in which the dilute aqueous composition also contains polyethylenimine having a molecular weight between about 10,000 and about 70,000.

6. A method of treating hair to improve the manageability thereof, which comprises initially contacting the hair with a dilute aqueous solution, clear to the naked eye, containing a water-soluble quaternary ammonium compound containing at least one long chain alkyl radical attached to the central nitrogen atom thereof, N-ethanolacetamide, polyethylenimine having a molecular weight between about 10,000 and about 70,000, and at least one acid selected from the group consisting of formic acid and acetic acid having a pH in the range of about 3 to below 7, and subsequently shampooing the hair with an anionic shampoo.

7. The method of claim 6, in which the dilute aqueous solution contains the stated ingredients in approximately the following proportions by weight of said solution:

| | |
|---|---|
| Water | 70 to 90% |
| Quatenary ammonium compound | 0.5 to 4% |
| N-Ethanolacetamide | 3 to 18% |
| Polyethylenimine | 0.5 to 5%. |

8. A composition for pretreatment of hair prior to shampooing said pretreated hair with an anionic shampoo, said composition comprising a major proportion of water, and minor proportions of a readily water-soluble quaternary ammonium compound containing at least one long chain alkyl radical attached to the central nitrogen atom thereof and polyethylenimine having a molecular weight in the range of about 10,000 to about 70,000.

9. The composition according to claim 8, which also includes a minor proportion of at least one member of the group of N-ethanolacetamide and a fatty acid ethanolamide in which the fatty acid comprises predominately lauric acid.

10. The composition of claim 8, which also includes at least one water-soluble acid and has a pH in the range of about 3 to below 7.

11. A composition according to claim 8, in which the quaternary ammonium compound has the formula

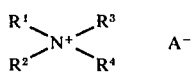

wherein $R^1$ is $C_8$–$C_{18}$ alkyl; each of $R^2$, $R^3$ and $R^4$ is $C_1$–$C_3$ alkyl, the total number of carbon atoms in $R^2$, $R^3$ and $R^4$ not exceeding 6; and A is an innocuous anion.

12. The composition according to claim 11, wherein $R^1$ is predominately dodecyl; each of $R^2$, $R^3$ and $R^4$ is methyl; and A is chlorine or bromine.

13. The composition of claim 10, in which the acid is formic acid or acetic acid.

14. A composition for pretreatment of hair prior to shampooing said pretreated hair with an anionic shampoo, said composition containing from about 70 to about 90% of water, from about 0.5 to about 4% of a readily water-soluble quaternary ammonium compound containing at least one long chain alkyl radical attached to the central nitrogen atom thereof, from about 3 to 18% of N-ethanolacetamide, and from about 0.2 to 5% of polyethylenimine having a molecular weight in the range of about 10,000 to about 70,000, said percentages being by weight of the composition.

15. A composition for pretreatment of hair prior to shampooing said pretreated hair with an anionic shampoo, said composition comprising a clear aqueous solution containing from about 70 to about 90% of water, from about 0.5 to about 4% of a readily water-soluble quaternary ammonium compound having the formula

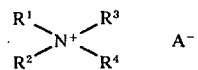

where $R^1$ is alkyl containing predominately from 10 to 14 carbon atoms; $R^2$, $R^3$ and $R^4$ are each methyl; and A is chlorine or bromine; from about 3 to 18% of N-ethanolacetamide, and from about 0.2 to 2% of polyethylenimine having a molecular weight between about 10,000 and about 70,000, said percentages being by weight of the composition.

16. A composition for pretreatment of hair prior to shampooing said pretreated hair with an anionic shampoo, said composition comprising a clear aqueous solution containing from about 70 to about 85% of water, from about 1.5 to about 2% of a readily water-soluble quaternary ammonium compound having the formula

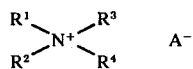

where $R^1$ is alkyl containing predominately from 10 to 14 carbon atoms; $R^2$, $R^3$ and $R^4$ are each methyl; and A is chlorine or bromine; from about 12 to 15% of N-ethanolacetamide, and from bout 1 to 2% of polyethylenimine having a molecular weight between about 40,000 to about 60,000, said percentages being by weight of the composition.

17. The composition according to claim 16, which also includes at least one water-soluble acid and has a pH in the range of about 3 to below 7.

18. The composition of claim 17, in which the acid is formic acid or acetic acid.

* * * * *